United States Patent [19]

Weber et al.

[11] 4,100,026
[45] Jul. 11, 1978

[54] PROCESS FOR THE PREPARATION OF 4-ANDROSTENE-3,17-DIONE DERIVATIVES

[75] Inventors: Alfred Weber; Mario Kennecke; Rudolf Mueller; Ulrich Eder; Rudolf Wiechert, all of Berlin, Fed. Rep. of Germany

[73] Assignee: Schering Aktiengesellschaft, Berlin and Bergkamen, Fed. Rep. of Germany

[21] Appl. No.: 751,677

[22] Filed: Dec. 17, 1976

[30] Foreign Application Priority Data

Dec. 19, 1975 [DE] Fed. Rep. of Germany ....... 2558090

[51] Int. Cl.$^2$ ............................................. C07B 29/00
[52] U.S. Cl. ................................................. 195/51 G
[58] Field of Search ..................................... 195/51 G

[56] References Cited
U.S. PATENT DOCUMENTS

| | | | |
|---|---|---|---|
| 3,388,042 | 6/1968 | Arima et al | 195/51 G |
| 3,684,656 | 8/1972 | Waard | 195/51 G |
| 3,759,791 | 9/1973 | Marsheck et al | 195/51 G |

*Primary Examiner*—Alvin E. Tanenholtz
*Attorney, Agent, or Firm*—Millen & White

[57] ABSTRACT

A process for the preparation of 4-androstene-3,17-dione derivatives of the formula

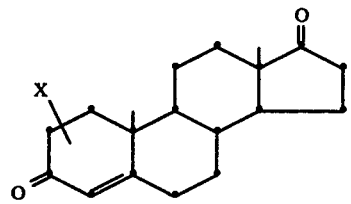

wherein X is 1,2-methylene or 1- or 2-methyl, comprises fermenting a sterol derivative of the formula

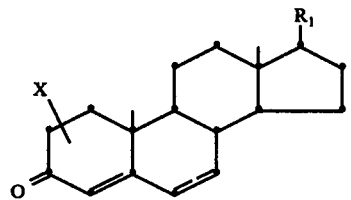

wherein X is as above, the bond$===$ is a single or double bond, and $R_1$ is the hydrocarbon residue, of 8–10 carbon atoms, of a sterol, with a microorganism culture capable of the side chain degradation of sterols.

10 Claims, No Drawings

PROCESS FOR THE PREPARATION OF 4-ANDROSTENE-3,17-DIONE DERIVATIVES

BACKGROUND OF THE INVENTION

Numerous microorganisms, for example of the genera Arthrobacter, Brevibacterium, Microbacterium, Protaminobacter, Bacillus, Norcardia, or Streptomyces, especially Mycobacterium, are capable of degrading zoosterols and phytosterols to carbon dioxide and water. During this degradation, 4-androstene-3,17-dione and 1,4-androstadiene-3,17-dione are formed as intermediates.

It is possible, by using inhibiting additives or mutated microorganisms, to control degradation of the sterols to prevent further degradation of the thus-formed 4-androstene-3,17-dione or 1,4-androstadiene-3,17-dione. See DOS's (German Unexamined Laid-Open Applications) Nos. 1,543,269 and 1,593,327, and U.S. Pat. 3,684,657.

SUMMARY OF THE INVENTION

A process for the preparation of a 4-androstene-3,17-dione compound of Formula I

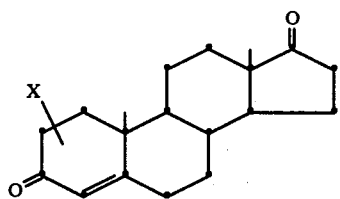

wherein X is 1,2-methylene or 1- or 2-methyl, comprising fermenting a sterol of Formula II

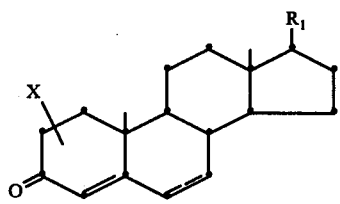

wherein X is as above, ----- is a single or double bond, and $R_1$ is a saturated or unsaturated hydrocarbon side chain of 8–10 carbon atoms, with a microorganism culture capable of degrading the side chain.

DETAILED DESCRIPTION

Hydrocarbon residue $R_1$ of 8–10 carbon atoms is an unsaturated or hydrogenated side chain of a naturally occurring zoosterol or phytosterol, e.g., cholesterol, stigmasterol, campesterol, brassicasterol, or the sitosterols.

Sterol compounds of Formula II include, for example, compounds of Formula IIa

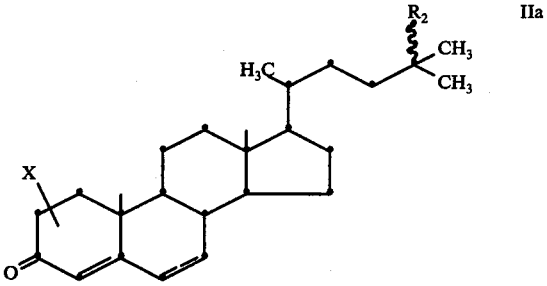

wherein X and ----- are as above and $R_2$ is hydrogen, methyl or ethyl.

Exemplary starting compounds for the process of this invention are sterols wherein X is 1α-methyl, 1β-methyl, 1α,2α-methylene, or 1β,2β-methylene. Examples of suitable starting compounds are:
  1α-methyl-4-cholesten-3-one,
  1β-methyl-4-cholesten-3-one,
  1α,2α-methylene-4-cholesten-3-one,
  1α,2α-methylene-4,5-cholestadien-3-one,
  1α-methyl-4-stigmasten-3-one,
  1α,2α-methylene-4-stigmasten-3-one,
  1α,2α-methylene-4,6-stigmastadien-3-one, or the corresponding sitosterol derivatives.

Other than the use of different starting compounds and the fact that the reaction is done in the absence of inhibitors, the process of the present invention is accomplished under the same fermentation conditions utilized in conventional microbiological side chain degradation reactions of sterols.

The fermentation is conducted using microorganism cultures customarily employed for the side chain degradation of sterols. Suitable cultures are, for example, those of the genera Arthrobacter, Brevibacterium, Microbacterium, Protaminobacter, or Streptomyces. Those of the genus Mycobacterium are preferred.

Examples of suitable microorganisms are: Microbacterium lactum IAM-1640, Protaminobacter alboflavus IAM-1040, Bacillus roseus IAM-1257, Bacillus sphaericus ATCC-7055, Norcardia gardneri IAM-105, Norcardia minima IAM-374, Norcardia corallina IFO-3338, Streptomyces rubescens IAM-74 or especially the microorganisms Mycobacterium avium IFO-3082, Mycobacterium phlei IFO-3158, Mycobacterium phlei (Institute of Health, Budapest No. 29), Mycobacterium phlei ATCC-354, Mycobacterium smegmatis IFO-3084, Mycobacterium smegmatis ATCC-20, Mycobacterium smegmatis (Institute of Health, Budapest No. 27), Mycobacterium smegmatis ATCC-19979, Mycobacterium fortuitum CBS-49566, Mycobacterium spec. NRRL-B-3805, and Mycobacterium spec. MRRL-B-3683. Mycobacterium spec. NRRL-B-3805 is most preferred.

Submerged cultures are grown under conditions customarily employed for these microorganisms, using a suitable nutrient medium with aeration. Then, the substrate, dissolved in a suitable solvent or preferably in emulsified form, is added to the culture and the fermentation is conducted until maximum substrate conversion has been attained.

Suitable solvents for the substrate are, for example, methanol, ethanol, glycol monomethyl ether, dimethylformamide, or dimethyl sulfoxide. The substrate can be emulsified, for example, by adding micronized substrate or substrate dissolved in a water-miscible solvent, e.g., methanol, ethanol, acetone, glycol monomethyl ether, dimethylformamide, or dimethyl sulfoxide, through nozzles under strongly turbulent conditions, to, preferably decalcified, water containing the customary emulsifying agents. Suitable emulsifying agents include non-ionic emulsifiers, for example, ethylene oxide adducts or fatty acid esters of polyglycols. Examples of suitable emulsifiers are surfactants commercially available, as "Tegin", "Tagat", "Tween", and "Span".

The optimum substrate concentration, time of substrate addition, and duration of fermentation depend on the structure of the substrate employed and on the type of the microorganism utilized. These variables must be determined in each individual case, by preliminary experiments well-known to those skilled in the art.

References to fermentation techniques include (G. S. Fonken and R. A. Johnson: Chemical Oxydations with Microorganism: Macel Dekker Inc., New York, 1972.

It is surprising to those skilled in the art that, under otherwise conventional conditions, the side chains of sterols of Formula II are degraded, because it is known that side chain degradation of sterols is effected by a very complex fermentation system. It therefore could not be expected that all of the enzymes taking part in side chain degradation of natural steroids would also cause degradation of the side chain of sterols of Formula II, which do not occur in nature. Moreover, it could not be foreseen that enzyme systems effecting degradation of 1,4-androstadiene-3,17-dione and 4-androstene-3,17-dione would be incapable of further degrading 4-androstene-3,17-dione compounds of Formula I.

Another surprising aspect of the fermentative reaction of sterols of Formula II with a $\Delta^6$-double bond is hydrogenation of the latter.

The 4-androstene-3,17-dione compounds of Formula I which can be produced according to the process of this invention are valuable intermediates for the synthesis of pharmacologically active steroids, e.g., 17β-hydroxy-1α-methyl-5α-androstan-3-one, 17β-hydroxy-1-methyl-5α-androst-1en-3-one, 2α-methyl-17β-propionyloxy-5α-androstan-3-one and 1,2α-methylene-17α-hydroxy-4,6-pregnadiene-3,20-dione.

It is possible, for example, to reduce the 17-keto group of the 4-androstene-3,17-dione derivatives, optionally after ketalization of the 3-oxo group, or to react the 17-keto group with an organometallic compound of the formula MeR$_4$, wherein R$_4$ is alkyl, alkenyl or alkynyl of up to 4 carbon atoms and Me is an alkali metal atom or a magnesium halide residue, to obtain, after splitting off the ketal group which may be present, 17β-hydroxy-4-androsten-3-one compounds of Formula III

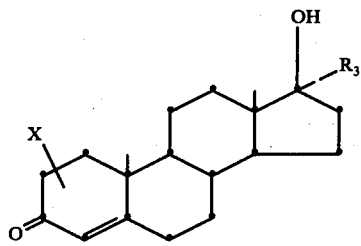

wherein X is as above and R$_3$ is R$_4$ or hydrogen.

R$_4$ alkyl, alkenyl or alkinyl is preferably methyl, ethyl, vinyl, or ethynyl.

Reduction of the 17-keto group of 4-androstene-3,17-dione derivatives of Formula I is effected by methods well-known to those skilled in the art. See, for example, John Fried: Organic Reactions in Steroid Chemistry, van Nostrand Reinhold Comp., New York, etc. (1972) 1 : 61 et seq. These compounds can be reacted, for example, after ketalization with sodium borohydride or lithium aluminum hydride. After splitting of the ketals, the corresponding 17β-hydroxy-4-androsten-3-one derivatives of Formula III are obtained. These are known to possess anabolic and/or androgenic activity.

Methods for alkylating the 17-keto group are likewise conventional. See, for example, John Fried: Organic Reactions in Steroid Chemistry, van Nostrand Reinhold Comp., New York, etc. (1972) 2 : 53 et seq. 4-Androstene-3,17-dione derivatives of Formula I can be reacted, optionally after ketalization of the 3-oxo group, for example, with alkyl magnesium halides, vinyllithium, or alkali metal acetylides. After splitting the ketal group which may be present, 17αR-17β-hydroxy-4-androsten-3-one derivatives of Formula III are obtained. These are pharmacologically active substances or intermediates for the preparation of pharmacologically active steroids, e.g., 17β-hydroxy-17α-methyl-5α-androstan-3,2 c-pyrazole.

Sterol derivatives of Formula II can be prepared from the corresponding sterols by methods conventionally employed for introduction of the corresponding 1- and/or 2-substituents into steroids. See, for example, John Friend and John A. Edwards: Organic Reactions in Steroid Chemistry; van Nostrand Reinhold Comp. New York, 1972.

The following examples serve for explaining the invention.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

(A) Examples Concerning the Microbiological Side Chain Degradation

EXAMPLE 1

A 2-liter Erlenmeyer flask with 500 ml. of a sterile nutrient medium, containing 1% yeast extract, 0.45% disodium hydrogen phosphate, 0.34% potassium dihydrogen phosphate, and 0.2% "Tween" 80, adjusted to pH 6.7, is inoculated with a suspension of a Mycobacterium spec. NRRL-B-3805 dry culture and shaken for 3 days at 30° C. at 190 r.p.m.

Twenty Erlenmeyer flasks each containing 100 ml. of a sterile nutrient medium, containing 2.0% corn steep liquor, 0.3% diammonium hydrogen phosphate, and 0.25% "Tween" 80, adjusted to pH 6.5, are inoculated with 5 ml. portions of the Mycobacterium spec. growth culture and shaken at 30° C. for 24 hours with 220 r.p.m.

Then, each culture is combined with 100 mg. of 1α,-2α-methylene-4,6-cholestadien-3-one, dissolved in 1 ml. of dimethylformamide, and the mixture is fermented for another 96 hours at 30° C.

The combined cultures are extracted with ethylene chloride; the extract is concentrated under vacuum, the residue is purified by chromatography over a silica gel column, and, after recrystallization from diisopropyl ether, 0.9 g. of 1α,2α-methylene-4-androstene-3,17-dione is obtained, m.p. 155° C.

PREPARATION OF THE STARTING COMPOUND:

(a) 111 g. of 3β-hydroxy-5-cholestene is heated in 2.2 l. of toluene and 111 ml. of cyclohexane to boiling. A solution of 55.5 g. of aluminum isopropylate in 666 ml. of toluene is added dropwise thereto. The mixture is then further heated for 90 minutes with gradual distillation. The cooled reaction solution is diluted with ether, washed with dilute sulfuric acid and water, and concentrated. The residue is distilled with steam and the crude product, obtained after extraction with methylene chloride, is chromatographed on silica gel. After recrystallization from methanol, 70 g. of 4-cholesten-3-one is obtained, m.p. 79° – 80.5° C.

(b) 60 g. of 4-cholesten-3-one is dissolved in 2 l. of ether and 1 ml. of hydrobromic acid in acetic acid, 37% strength. It is combined, with agitation, with a solution of 52.4 g. of bromine in 300 ml. of acetic acid. The mixture is then further stirred for 15 minutes, thereafter diluted with a small quantity of ether, and washed in succession with water, sodium bicarbonate solution, and water. After drying and evaporation, 90 g. of crude 2,6-dibromo-4-cholesten-3-one is obtained in the form of an oil.

(c) 90 g. of crude 2,6-dibromo-4-cholesten-3-one is agitated in 900 ml. of dimethylformamide with 36.9 g. of lithium carbonate and 43.3 g. of lithium bromide for 20 hours at 100° C. The mixture is then stirred into ice water, the precipitate is filtered off, washed with water, and taken up in methylene chloride. After drying and evaporation, the residue is chromatographed on silica gel, thus obtaining 42 g. of 1,4,6-cholestatrien-3-one as an oil.

(d) 31.9 g. of trimethyl sulfoxonium iodide is agitated in 1 l. of dimethyl sulfoxide with 5.6 g. of pulverized sodium hydride for 2 hours at room temperature. This solution is then added to 40 g. of 1,4,6-cholestatrien-3-one, dissolved in 200 ml. of absolute tetrahydrofuran, and agitated for 24 hours at room temperature. The mixture is stirred into acetic ice water and decanted off from the separated oil. The latter is taken up in ether. After drying and evaporation, chromatography, and recrystallization from methanol, the yield is 10.5 g. of 1α,2α-methylene-4,6-cholestadien-3-one, m.p. 68-69° C.

EXAMPLE 2

Under the conditions of Example 1, 100 mg. portions of 1α-methyl-4-cholesten-3-one are reacted in twenty Erlenmeyer flasks with a Mycobacterium spec. NRRL-B-3805 culture and worked up. The yield is 1α-methyl-4-androstene-3,17-dione, m.p. 134-137° C.

The 1α-methyl-4-cholesten-3-one, utilized as the starting compound, is known (C.A. 61, (1964) 8367 et seq.).

(B) Examples Concerning the Chemical Further Processing of the 4-Androstene-3,17-dione Derivatives

EXAMPLE 1

3.2 g. of 1α,2α-methylene-4-androstene-3,17-dione is dissolved in 50 ml. of absolute ethanol, cooled to 0° C., and mixed with 0.5 g. of sodium borohydride in incremental portions. After a reaction period of 3 hours with ice cooling. The mixture is stirred into 50 ml. of semisaturated sodium dihydrogen phosphate solution. The thus-precipitated product is filtered off and washed with water. After recrystallization from ethanol, 1.95 g. of 17β-hydroxy-1α,2α-methylene-4-androsten-3-one is obtained and gives after acetylation with acetic anhydridepyridine at room temperature, strongly anabolic 17β-acetoxy-1α,2α-methylene-4,6-androsten-3-one, "Arzneim. Forschung" (Drug Research) 15 (1965) : 1168.

EXAMPLE 2

Under the conditions of Example 1, 1α-methyl-4-androstene-3,17-dione is converted into the strongly anabolically effective 17β-acetoxy-1α-4-androsten-3-one "Arzneim. Forschung" 15 (1965) : 1168.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a 4-androstene-3,17-dione compound of the formula

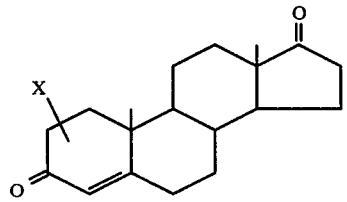

wherein X is 1,2-methylene or 1- or 2-methyl, comprising fermenting, in the absence of 4-androstene-3,17-dione degradation inhibitors, a sterol of the formula

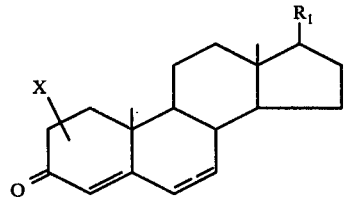

wherein X is as above, ——— is a single or double bond, and $R_1$ is a saturated or unsaturated hydrocarbon side chain of 8-10 carbon atoms, with a microorganism culture capable of degrading sterol side chains.

2. The process of claim 1, comprising the further step of either (a) selectively reducing the 17-keto group of the thus-produced 4-androstene-3,17-dione; or (b) selectively reacting the 17-keto group of the thus-produced 4-androstene-3,17-dione with an organometallic compound of the formula MeR$_4$, wherein R$_4$ is alkyl, alkenyl or alkinyl of up to 4 carbon atoms and Me is an alkali metal atom or magnesium halide residue to produce a 17β-hydroxy-4-androsten-3-one compound of the formula

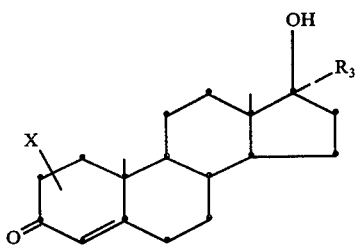

wherein X is 1,2-methylene or 1- or 2-methyl and $R_3$ is hydrogen or $R_4$, respectively.

3. The process of claim 2, comprising the additional steps of ketalizing the carbonyl at the 3-position of the 4-androstene-3,17-dione compound prior to the selective reduction or selective reaction and subsequently cleaving the ketal at the 3-position of the 17β-hydroxy-4-androsten-3-one compound after the selective reduction or selective reaction.

4. The process of claim 2, wherein $R_3$ is hydrogen, methyl, ethyl, vinyl or ethynyl.

5. The process of claim 1, wherein the microorganism culture is of genera Arthrobacter, Brevibacterium, Microbacterium, Protaminobacter, Bacillus, Norcardia or Streptomyces.

6. The process of claim 1, wherein the microorganism culture is of the genus Mycobacterium.

7. The process of claim 1, wherein the microorganism culture is Mycobacterium spec. NRRL-B-3805.

8. The process of claim 2, wherein the microorganism culture is of genera Arthrobacter, Brevibacterium, Microbacterium, Protaminobacter, Bacillus, Norcardia or Streptomyces.

9. The process of claim 2, wherein the microorganism culture is of the genus Mycobacterium.

10. The process of claim 2, wherein the microorganism culture is Mycobacterium spec. NRRL-B-3805.

* * * * *